United States Patent [19]

Stamatoyannopoulos

[11] Patent Number: 4,965,251

[45] Date of Patent: Oct. 23, 1990

[54] PULSE TREATMENT OF HEMOGLOBINOPATHIES WITH ERYTHROPOIETIN

[75] Inventor: George Stamatoyannopoulos, Seattle, Wash.

[73] Assignee: The Board of Regents of The University of Washington, Seattle, Wash.

[21] Appl. No.: 34,309

[22] Filed: Apr. 3, 1987

[51] Int. Cl.$^5$ ............................................. A61K 37/02
[52] U.S. Cl. .......................................... 514/8; 514/2; 514/21; 530/350; 530/380; 530/395
[58] Field of Search .................... 514/8, 2, 21; 424/99, 424/101; 530/380, 397, 350

[56] References Cited

U.S. PATENT DOCUMENTS

| | | | |
|---|---|---|---|
| 3,865,801 | 2/1975 | Chiba et al. | 424/99 |
| 4,303,650 | 12/1981 | Takezawa et al. | 530/397 |
| 4,397,840 | 8/1983 | Takezawa et al. | 424/99 |
| 4,568,488 | 2/1986 | Lee-Huang | 424/99 |
| 4,677,195 | 6/1987 | Hewick et al. | 530/397 |
| 4,703,008 | 10/1987 | Lin | 435/240.2 |

OTHER PUBLICATIONS

Essers et al., Proc. Eur. Dial. Transplant Ass'n, 11, 398–402, (1974).
Papayannopoulou, Th., et al., Fetal Hb production during acute erythroid expansion, Br. J. Haemat 44:535–546, 1980.
Alter, B.A., Fetal erythropoiesis in bone marrow failure syndromes, in Cellular and Molecular Regulation of Hemoglobin Switching, G. Stamatoyannopoulos and A. W. Nienhuis, Eds., Grune and Stratton, N.Y., pp. 87–105, 1979.
Dover, G. J., et al., Production of erythrocytes that contain fetal hemoglobin in anemia: transient in vivo changes, J. Clin. Invest. 63:173–176, 1979.
Desimone, J., et al., Stimulation of fetal hemoglobin synthesis in baboons by hemolysis and hypoxia, Proc. Natl. Acad. Sci. (USA) 75(6):2937–2940, 1978.
Nute, P. E., et al., Acceleration of F—cell production in response to experimentally induced anemia in adult baboons (Papio cynocephalus), Am. J. Hematal. 8:157–168, 1980.
Dover, C. J., et al., Progress toward incresing fetal hemoglobin production in man: experience with 5—azacytidine and hydroxyurea, Ann. N.Y. Acad. Sci. 445:218–224, 1985.
Stamatoyannopoulos, G., and A. W. Nienhuis, Hemoglobin switching, in The Molecular Basis of Blood Diseases, G. Stamatoyannopoulos, et al., Eds., W. B. Saunders Company, pp. 66–105, 1987.
McGonigle et al., Kidney, Int., 25, 437–44, (1984).
Pavlovic-Kentera et al., Biol. Abs., 73(1), p. 62, Abs. 587, (1982)
Eschbach et al., J. Clin. Invest., 74, 434–41, (1984).
Egrie et al., Biol. Abs., 83(5), p. Ab. 317, Abs. #92648, (1986 (pub. date)).

(List continued on next page.)

*Primary Examiner*—Margaret Moskowitz
*Assistant Examiner*—Jeff Kushan
*Attorney, Agent, or Firm*—Christensen, O'Connor, Johnson & Kindness

[57] ABSTRACT

A method of treating a hemoglobinopathic condition such as sickle cell anemia, by pulse treatment with erythropoietin. In one embodiment, each of one or more treatment regimens includes a first time period during which erythropoietin is administered to a hemoglobinopathic patient and a second time period during which erythropoietin is withheld from the patient. During the first time period, sufficient erythropoietin is administered to increase F-reticulocyte formation in the patient. The pulse treatment preferably includes a plurality of the treatment regimens, in which case the durations of the second time periods are selected to achieve a cumulative increment of F-cell count sufficient to effectively treat the patient's hemoglobinopathic condition. In another embodiment, the erythropoietin treatment regimens are alternated with similar pulse treatments using a cell cycle specific drug such as hydroxyurea.

13 Claims, 5 Drawing Sheets

OTHER PUBLICATIONS

Stamatoyannopoulos, G., and Th. Papayannopoulou, Fetal hemoglobin and the erythroid stem cell differentiation process, in Cellular and Molecular Regulation of Hemoglobin Switching, G. Stamatoyannopoulous and A. W. Nienhuis, Eds., Grune & Stratton, New York, pp. 323–350, 1979.

Stamatoyannopoulos, G., et al., Hb F production in stressed erythropoiesis: observations and kinetic models, Ann. N.Y. Acad. Sci. 445:188–197, 1985.

DeSimone, J., et al., 5-Azacytidine stimulates fetal hemoglobin synthesis in anemic baboons, Proc. Natl. Acad. Sci. (USA) 79:4428–4431, 1982.

Torrealba—de Ron, A. T., et al., Perturbations in the erythroid marrow progenitor cell pools may play a role in the augmentation of HbF by 5—azacytidine, Blood 63(1):201–210, 1984.

Ley, T. J., et al., 5—Azacytidine selectively increases gammaglobin synthesis in a patient with beta+ thalassemia, N. Engl. J. Med. 307(24):1469–1475, 1982.

Ley, T. J., et al., 5—Azacytidine increases gamma--globin synthesis and reduces the proportion of dense cells in patients with sickle cell anemia, Blood 62(2):370–380, 1983.

Nienhuis, A. W., et al., Pharmacological manipulation of fetal hemoglobin synthesis in patients with severe beta—Thalassemia, Ann. N.Y. Acad. Sci. 445:198–211, 1985.

Charache, S., et al., Treatment of sickle cell anemia with 5—azacytidine results in increased fetal hemoglobin production and is associated with nonrandom hypomethylation of DNA around the gamma-delta-globin gene complex, Proc. Natl. Acad. Sci. (USA) 80:4842–4846, 1983.

Humphries, R. K., et al., 5—Azacytidine acts directly on both erythroid precursors and progenitors to increase production of fetal hemoglobin, J. Clin. Invest. 75:547–557, 1985.

Dover, G. J., et al., 5—Azacytidine increases HbF production and reduces anemia in sickle cell disease: dose—response analysis of subcutaneous and oral dosage regimens, Blood 66(3):527–532, 1985.

Papayannopoulou, Th., et al., Arabinosylcytosine induces fetal hemoglobin in baboons by perturbing erythroid cell differentiation kinetics, Science 224:617–619, 1984.

Letvin, N. L., et al., Augmentation of fetal—hemoglobin production in anemic monkeys by hydroxyurea, New Engl. J. Med. 310(14):869–873, 1984.

Platt, O. S., et al., Hydroxyurea enhances fetal hemoglobin production in sickle cell anemia, J. Clin. Invest. 74:652–656, 1984.

Veith, R., et al., Stimulation of F—cell production in patients with sickle—cell anemia treated with cytarabine or hydroxyurea, N. Engl. J. Med. 313(25):1571–1575, 1985.

Dover, G. J., et al., Hydroxyurea induction of hemoglobin F production in sickle cell disease: relationship between cytotoxicity and F cell production, Blood 67(3):735–738, 1986.

Charache, S., et al., Hydroxyurea—induced augmentation of fetal hemoglobin production in patients with sickle cell anemia, Blood 69(1):109–116, 1987.

Veith, R., et al., Treatment of baboon with vinblastine: insights into the mechanisms of pharmacologic stimulation of HbF in the adult, Blood 66(2):456–459, 1985.

Spivak, J. L., The mechanisms of action of erythropoietin, Intl. J. Cell Cloning 4:139–166, 1986.

Papayannopoulou, Th., et al., On the in vivo action of erythripoietin: quantative analysis, J. Clin. Invest. 51:1179–1185, 1972.

Papayannopoulou, Th., et al., Hemoglobin F synthesis in vitro: evidence for control at the level of primitive erythroid stem cells, Proc. Natl. Acad. Sci. (USA) 74(7):2923–2927, 1977.

Macklis, R. M., et al., Synthesis of hemoglobin F in adult simian erythroid progenitor—derived colonies, J. Clin. Invest. 70:752–761, 1982.

Torrealba de Ron, A., et al., Studies of HbF in adult non—anemic baboons: HbF expression in erythroid colonies decreases as the level of maturation of erythroid progenitors advances, Exp. Hematol. 13:919–925, 1985.

Adamson, J. W., et al., Activation of hemoglobin C synthesis in sheep marrow culture, Science 180:310–312, 1973.

Nienhuis, A. W., et al., Induction of hemoglobin C synthesis in sheep: characterization of the "switching" stem cell, in Cellular and Molecular Regulation of Hemoglobin Switching, G. Stamatoyannopoulos and A.

(List continued on next page.)

OTHER PUBLICATIONS

W. Nienhuis, Eds., Grune & Stratton, New York, pp. 397–420, 1978.

Papayannopoulou, Th., et al., Cellular regulation of hemoglobin switching: evidence for inverse relationship between fetal hemoglobin synthesis and degree of maturity of human erythroid cells, Proc. Natl. Acad. Sci. (USA) 76(12):6420–6424, 1979.

Eschbach, J. W., et al., Correction of the anemia of end–stage renal disease with recombinant human erythropoietin, N. Eng. J. Med. 316(2):73–78, Jan. 1987.

Winearls, C. G., et al., Effect of human erythropoietin derived from recombinant DNA on the anaemia of patients maintained by chronic haemodialysis, The Lancet ii:1175–1178, Nov. 1986.

Alter, B. P., et al., Fetal erythropoiesis following bone marrow transplantation, Blood 48():843–852, 1976.

Amylon et al., Am. J. Hematol,, 23, 179–81, (1986).

PULSE TREATMENT OF HEMOGLOBINOPATHIES WITH ERYTHROPOIETIN

This invention was made partly with government support under one or more of grants HL20899 and HL21676 from the National Institutes of Health. The government has certain rights in this invention.

TECHNICAL FIELD

This invention relates to therapeutic methods of treating those anemias (hemoglobinopathies) such as sickle cell anemia that are caused by defective hemoglobin synthesis.

BACKGROUND OF THE INVENTION

Fetal hemoglobin (Hb F) is present at birth, gradually decreases in the first months of life, and normally makes up less than 2% of total hemoglobin in adults. The normal adult hemoglobin molecule (Hb A; $\alpha_2 \beta_2$) consists of two pairs of polypeptide chains designated and $\beta$. In fetal hemoglobin ($\alpha_2 \gamma_2$), $\gamma$ chains are substituted for the $\beta$ chains. The types of hemoglobin chains and the chemical structure of individual polypeptides in the chains are controlled genetically. Genetic defects may result in hemoglobin molecules with abnormal physical or chemical properties, some of which may result in anemia. Such anemias, termed hemoglobinopathies, are severe in homozygotes and relatively mild in heterozygous carriers. The abnormal hemoglobins are distinguished by their electrophoretic mobility and have been designated by letters. The first to be discovered was sickle cell hemoglobin (Hb S). The important hemoglobinopathies in the Untied States are those due to Hb S, Hb C, the thalassemias, and combinations thereof.

In sickle cell anemia (Hb S Disease), valine is substituted for glutamic acid in the sixth amino acid of the $\beta$ chain. As a result, deoxy-Hb S is much less soluble than the normal deoxy-Hb A, and the patient's red blood cells (erythrocytes) become sickle-shaped at sites of low oxygen concentration. The distorted erythrocytes are unable to pass through small arterioles and capillaries, and plugs of such sickled erythrccytes lead to thrombosis and infarction. This leads to crises of pain which last for several days. Sickled erythrocytes are also more fragile than normal erythrocytes and less able to withstand the mechanical trauma caused by circulation in blood. Few homozygous patients live beyond age 40. Therapy has traditionally been symptomatic, e.g., transfusions are given for symptomatic anemia.

Hemoglobin S-C Disease is a moderately severe anemia due to an inherited abnormality of hemoglobin formation in which half the hemoglobin is the S type and half is of type C. There is no specific treatment.

The thalassemias are a group of chronic, familial, hemolytic anemias characterized by defective hemoglobin synthesis and ineffective erythropoiesis. $\beta$-Thalassemia results from a decreased synthesis of $\beta$ polypeptide chains. Homozygotes ($\beta$-thalassemia major) typically have severe anemia (Cooley's anemia) from infancy, and many such patients do not survive to puberty. Treatment is typically by chronic transfusion to suppress the abnormal hematopoiesis, coupled with splenectomy to alleviate the hypertrophic spleen growth (splenomegaly) that is often consequent to such hemoglobinopathies.

Clinical and experimental evidence suggests that stimulation of fetal hemoglobin will benefit patients with sickle cell anemia. Fetal hemoglobin in the adult appears to be restricted to a subpopulation of cells, the F-cells, which originate from the same progenitors as the normal adult erythrocytes that do not contain fetal hemoglobin. The numbers of F-cells are elevated in several hemopoietic disorders. Formation of F-cells has been explained by various hypotheses, including premature commitment of erythroid progenitors. Stamatoyannopoulos, G., and Th. Papayannopoulou, in Cellular and Molecular Regulation of Hemoglobin Switching, G. Stamatoyannopoulos and A.W. Nienhuis, Eds., Grune & Stratton, New York, 1979, pp. 323–350; Stamatoyannopoulos, G., et al., Ann. NY Acad. Sci. 1985, 445: 188–197. According to the latter hypothesis, erythroid progenitor cells have the ability to form F-cells but fail to do so when the kinetics of erythroid maturation are normal; F-cells are formed when progenitor cells are forced to become erythroblasts prematurely, as in sudden bone marrow expansion or when there is a sudden acceleration of erythroid cell maturation kinetics.

Recently, several attempts have been made to stimulate fetal hemoglobin in animals and in patients with sickle cell disease. Stimulation of F-cell formation has been achieved with 5-azacytidine, a drug that induces $\gamma$-gene demethylation. DeSimone, J., et al., Proc. Natl. Acad. Sci. (USA) 1982, 79:4428–443; Torrealba de Ron, A., et al., Blood 1984, 63:201–210; Ley, T.J., et al., N. Engl. J. Med. 1982, 307:1469–1475; Ley, T.J., et al., Blood 1983, 62: 370–380; Nienhuis, A.W., et al., Ann. NY Acad. Sci. 1985, 445:198–211; Charache, S., et al., Proc. Natl. Acad. Sci. (USA) 1983, 80:4842–4846; Humphries, R.K., et al., J. Clin. Invest. 1985, 75:547–557; Dover, G.J., et al., Blood 1985, 66:527–532.Other cell cycle-specific drugs, such as hydroxyurea and cytarabine (Ara-C), have been found to stimulate F-cell formation in primates and human patients. Papayannopoulou, Th., et al., Science 1984, 224:617–619; Letvin, N.L., et al., New. Engl. J. Med. 1984, 310:869–873; Platt, O.S., et al., J. Clin. Invest. 1984, 74:652–656; Veith, R., et al., N. Engl. J. Med. 1986, 313:1571–1575; Dover, G.J., et al., Blood 1986, 67:735–738; Charache, S., et al., Blood 1987, 69:109–116. An M-stage compound, vinblastine, stimulates F-cell formation in baboons. Veith, R., et al., Br. J. Haemat. 1980, 44:535–546. The induction of fetal hemoglobin by cell cycle-specific drugs has been attributed to various mechanisms. One hypothesis is that the induced F-cell formation is due to the rapid erythroid regeneration kinetics triggered by the drug treatment.

Administration of erythropoietin in animals is associated with expansion of the erythroid progenitor and early precursor pools, with consequent stimulation of reticulocyte (young erythrocyte) production. Spivak, J.L., Intl. J. Cell Cloning 1986, 4:139–166; Papayannopoulou, Th., and C.A. Finch, J. Clin. Invest. 1972, 51:1179–1185. These effects are mainly due to the action of erythropoietin on late erythroid progenitors. Previous studies have shown that erythropoietin increases the number of fetal hemoglobin-positive colonies in human bone marrow cultures, induces fetal hemoglobin in cultures of monkey or baboon erythroid progenitors, and induces Hb C in sheep bone marrow cultures. Papayannopoulou, Th., et al., Proc. Natl. Acad. Sci. (USA) 1977, 74:2923–2927; Macklis, R.M., et al., J. Clin. Invest. 1982, 70:752; Torrealba de Ron, A., et al., Exp.

Hematol. 1985, 13:919-925; Adamson, J.W., et al., Science 1973, 80:310-312; Nienhuis, A.W., et al., in Cellular and Molecular Regulation of Hemoglobin Switching, G. Stamatoyannopoulos and A.W. Nienhuis, Eds., 1978, Grune & Stratton, New York, 397-420. These in vitro results most likely reflect effects of erythropoietin on the kinetics of in vitro erythroid cell differentiation. Direct induction of fetal hemoglobin synthesis by erythropoietin is not supported by previous results. Papayannopoulou, Th., et al., Proc. Natl. Acad. Sci. (USA) 1979, 76:6420-6424.

Recently, recombinant erythropoietin has been introduced in the treatment of humans. Eschbach, J.W., et al., N. Eng. J. Med. 1987, 316:73-78; Winerals, C.G., et al., Lancet 1986, ii:1175-1178.

Summary of the Invention

The invention provides a method of treating a hemoglobinopathic condition, such as sickle cell anemia or homozygous β-thalassemia, by pulse treatment with erythropoietin. The subject pulse treatment includes one or more treatment regimens. In one embodiment, each treatment regimen includes a first time period during which erythropoietin is administered to a hemoglobinopathic patient and a second time period during which erythropoietin is withheld from the patient. A relatively high dose of erythropoietin is administered in order to increase F-reticulocyte formation in the patient. To realize the full effects of the subject treatment, the pulse treatment should include a plurality of the treatment regimens. The durations of the second time periods are selected in order to achieve a continuous increment of F-reticulocyte formation to a level sufficient to effectively treat the patient's hemoglobinopathic condition, for example, sufficient to substantially inhibit vivo sickling of the patient's red blood cells. In another embodiment, the foregoing erthropoietin treatment regimens are alternated with similar pulse treatments using a cell cycle specific drug such as hydroxyurea.

DETAILED DESCRIPTION OF THE PREFERRED EMBODIMENT

Figure 1:
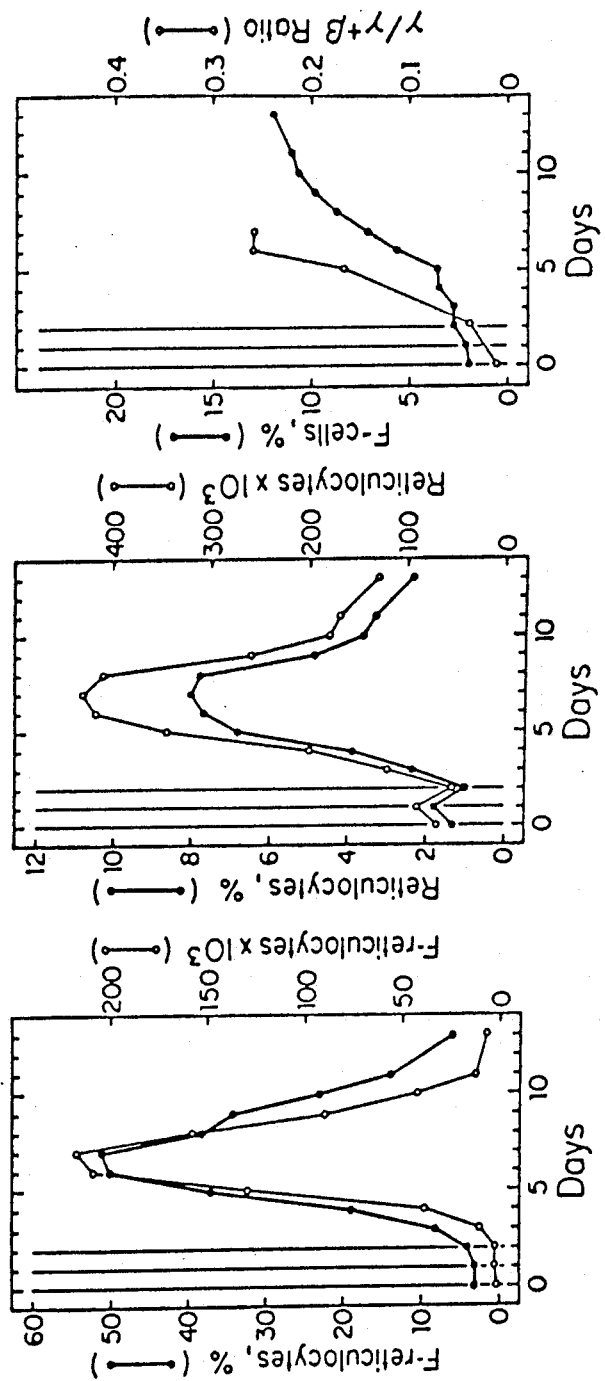
FIG. 1 presents experimental results achieved by treatment of a nonanemic baboon (animal A) with 1500 I.U. of recombinant erythropoietin per kg of body weight injected intravenously every 12 hours for 3 days, in terms of total reticulocytes (middle panel), fetal hemoglobin-containing reticulocytes (F-reticulocytes, left panel), and F-cell and $\gamma/\gamma+\beta$ biosynthetic ratios.

In the working examples described below and in the FIGURES, the administration of pulses of high doses of recombinant erythropoietin produced striking induction of F-cells in nonanemic and in anemic baboons. Nonanemic animals responded to the subject treatment with sharp increments of fetal hemoglobin-containing reticulocytes (F-reticulocytes) from 1-2% before treatment to 40-50% after treatment. Two chronically anemic animals with high levels of both F-cells and endogenous erythropoietin responded by increments of F-reticulocytes, respectively, from 6-8% preto 23% post-treatment and from 20% pre- to 50% posttreatment. Based on these results, it is contemplated that pulse treatment with erythropoietin will result in a considerable increment of F-cells in human patients with sickle cell anemia and other hemoglobinopathic conditions. For example, it is likely that sequential treatments spaced 10-15 days apart will result in accumulation of sufficient numbers of F-cells for inhibition of in vivo sickling. While the induction of F-cell formation will be beneficial, the erythropoietic effects of erythropoietin may not be, since significant elevations of the patients' hematocrits will tend to increase the chance for intravascular sickling. Increments in hematocrit, however, can be controlled by blood withdrawal, an intervention which will benefit patients with iron overload.

Thus, the invention provides a method of treating a hemoglobinopathic condition by pulse treatment with erythropoietin. The hemoglobinopathic condition may be any anemia caused by defective synthesis of adult hemoglobin ($\alpha_2$, $a_2$), including sickle cell anemia (Hemoglobin S Disease), Hemoglobin S-C Disease, β-thalassemia, paticularly β-thalassemia major (Cooley's anemia), and Hemoglobin S-Beta Thalassemia Disease. In one embodiment, the subject pulse treatment includes one or more treatment regimens, each treatment regimen having a first time period during which erythropoietin is admiministered to a hemoglobinopathic patient and a second time period during which erythropoietin is withheld from the patient. The dosage of erythropoietin administered during the first time period is selected to increase F-reticulocyte formation in the patient, preferably by twofold or more. Of course, the actual results achieved will depend to some extent upon the clinical condition of the patient. Similarily, the erythropoietin dosage and other treatment parameters will in practice be prescribed according to the best professional judgment of the attending physician. To realize the full effects of the subject treatment, the pulse treatment should include a plurality of the treatment regimens. In these sequential treatment regimens, the durations of the second time periods are individually selected to achieve an increment of F-cell count greater than that achievable by a single treatment regimen. For many patients, it is contemplated that the F-cell count can in this way be cumulatively increased to a level that is sufficient to effectively treat the patient's hemoglobinopathic condition. As an example, the subject pulse treatment may increase F-reticulocyte formation to a level sufficient to substantially inhibit in vivo sickling of a Hb S patient's red blood cells.

Typically, each of the human treatment regimens will individually have a duration of from about 7 to about 20 days. For the majority of patients, sequential treatment regimens of from about 10 to about 15 days each will achieve beneficial results, including but not limited to alleviation of painful crises associated with sickle cell anemia. Within treatment regimens of such length, typical first time periods will individually last from about to about 3 days, and preferably about one day. During each first time period, it is considered most advantageous, in terms of stimulating F-reticulocyte response, to administer the erythropoietin at least twice. Thus, the erythropoietin can be administered at from about 8 to about 24 hour intervals, and preferably at from about 12 to about 16 hour intervals, during each first time period. Each administration of erythropoietin should include from about 500 to about 3000 International Units (I.U.) erythropoietin per kg body weight of the patient. Dosages of from about 1000 to about 3000 I.U./kg, and most preferably about 1500 I.U./kg, are considered suitable for most patients. The erythropoietin is typically administered by intravenous injection, but intramuscular injection may also be employed. Due to its potential availability in the relatively enormous quantities required for the subject treatment, recombinant erythropoietin is presently preferred for practicing this invention. Of course, the invention can also be practiced with fragments or synthetic analogs of the erythropoietin hormone having, irrespective of their origin or method of production, the same or substantially similar effects upon F-reticulocyte formation when administered as described herein.

As mentioned, periodic phlebotomy (blood withdrawal) may be indicated as an adjunct treatment for Hb S (but not Cooley's anemia) patients in order to avoid substantial increase in hematocrit.

In another embodiment, the subject pulse treatment includes a plurality of treatment regimens, each having a first time period during which either erythropoietin or a cell cycle specific drug is administered to a hemoglobinopathic patient and a second time period during which the pharmaceutical reagent (erythropoietin or the cell cycle specific drug) is withheld from the patient. Suitable cell cycle specific drugs for this purpose include cytarabine (arabinosylcytosine), 5-azacytidine, and especially hydroxyurea. In the preferred embodiment, treatment regimens involving erythropoietin sequentially alternate with treatment regimens in which the cell cycle specific drug is administered. It is contemplated that the alternating pulsed effects upon F-reticulocytosis will produce a synegistic effect, in terms of producing a higher increment of F cells than either treatment regimen alone. In these alternating treatment regimens, the durations of the time periods and the dosage and injection schedules for the erythropoietin can be as described above. Dosages and injection schedules for the cell cycle specific drugs should be selected to stimulate F-reticulocyte formation with minimal toxicity. For this purpose, hydroxyurea can be administered by mouth at doses of from about 35 to about 50 mg per kg body weight per day for 1 to about 3 days. Cytarabine can be administered intravenously in daily administrations given over a period of about one hour at about 10 to about 45 mg per square meter of body-surface area per day for 1 to about 3 consecutive days.

Also provided are methods of manufacturing pharmaceutical reagents useful for treating hemoglobinopathies, in which a pharmaceutical reagent containing erythropoietin is packaged in combination with printed instructions for treating a hemoglobinopathic patient with any of the subject pulse treatments using the packaged reagent.

EXAMPLES

Materials and Methods

Baboons (1.5 to 4 years old) were treated with recombinant human erythropoietin (provided by Genetics Institute, Inc., Cambridge, MA) that was more than 99% pure and had a specific activity of 223,000 International Units (I.U.) per mg of protein. The erythropoietin (hereinafter "rHuEpo") was diluted in 5% glucose and 0.05% albumin. Each dose of erythropoietin was given intravenously over five minutes. Two animals were kept anemic by daily phlebotomy (removal of 7-10% of the animal's estimated blood volume). Anemic animals were supplemented with iron and folic acid, as described in Torrealba de Ron, A., et al., Blood 1984, 63:201-210.

Hematocrit, hemoglobin, red blood cells (RBC), white blood cells (WBC), and platelets were determined by a Coulter counter. Specimens for reticulocyte determination were prepared by incubating blood with 1% brilliant cresyl blue for 35 to 45 minutes; 2,000 cells were counted in the normal animals and 1,000 cells in the anemic animals. Cells containing fetal hemoglobin (F-cells) were measured in smears of washed red blood cells that were resuspended in fetal calf serum, allowed to dry, fixed in a mixture of acetone, methanol, and ethanol, and reacted with a murine anti-$\gamma$ monoclonal antibody and a goat antimouse (Fab)$_2$ fragment conjugated to fluorescein isothiocyanate (FITC). The fetal hemoglobin-containing reticulocytes (F-reticulocytes) were quantitated following immunochemical staining of reticulocyte preparations as described in Papayannopoulou, Th., et al., Br. J. Haemat. 1980, 44:535-546. For measurements of globin biosynthesis, reticulocyte-rich samples were incubated with $^3$H-leucine in leucine-free Iscove's Modified Dulbecco's Medium (IMDM) and 10% fetal calf serum at 37° C. overnight. At the end of incubation, the samples were washed, lysed, and used for isoelectric focusing of globin chains as described in Righetti, P.G., et al., J. Biochem. Biophys. Meth. 1979, 1:45-46. The relative proportions of synthesized globin chains ($\gamma/\gamma+\beta$) were determined by automated densitometry of the fluorograms.

Preliminary Results

In preliminary studies, a nonanemic animal was treated with 185 I.U. rHuEpo per kg per day $\times 6$; an anemic animal with 200 I.U. rHuEpo per kg every 12 hours $\times 4$; and a severely anemic animal with 600 I.U. per kg once. These treatments resulted in only small increases of F-cells. The further studies described below demonstrated that administration of higher doses o erythropoietin surprisingly produced significant induction of F-cells, and that pulse treatments produced a cumulative increment of F-cell count.

Stimulation of Hb F in nonanemic animals

Animal A had hematocrit of 39-40%, 1.5% reticulocytes, and 1.6% F-cells. This animal was treated with 1500 I.U. of rHuEpo per kg of body weight twice a day for 3 days. The response to this treatment is illustrated in FIG. 1. Days of treatment are indicated by vertical lines. Reticulocytes (shown in the middle panel) started increasing on day 3 and reached a maximum of 8% by day 7. Absolute reticulocytes were 50-70$\times 10^3$ per $\mu$l before treatment and 429$\times 10^3$ per $\mu$l 7 days post-treatment. A striking induction of fetal hemoglobin-containing reticulocytes was observed. F-reticulocytes (left panel) started increasing On day 4 and reached a maximum Of 50.7% of total reticulocytes by day 7. The $\gamma/\gamma+\beta$ ratio, which was less than 0.01 before treatment, increased to 0.26 by day 6 (right panel).

Figure 2:
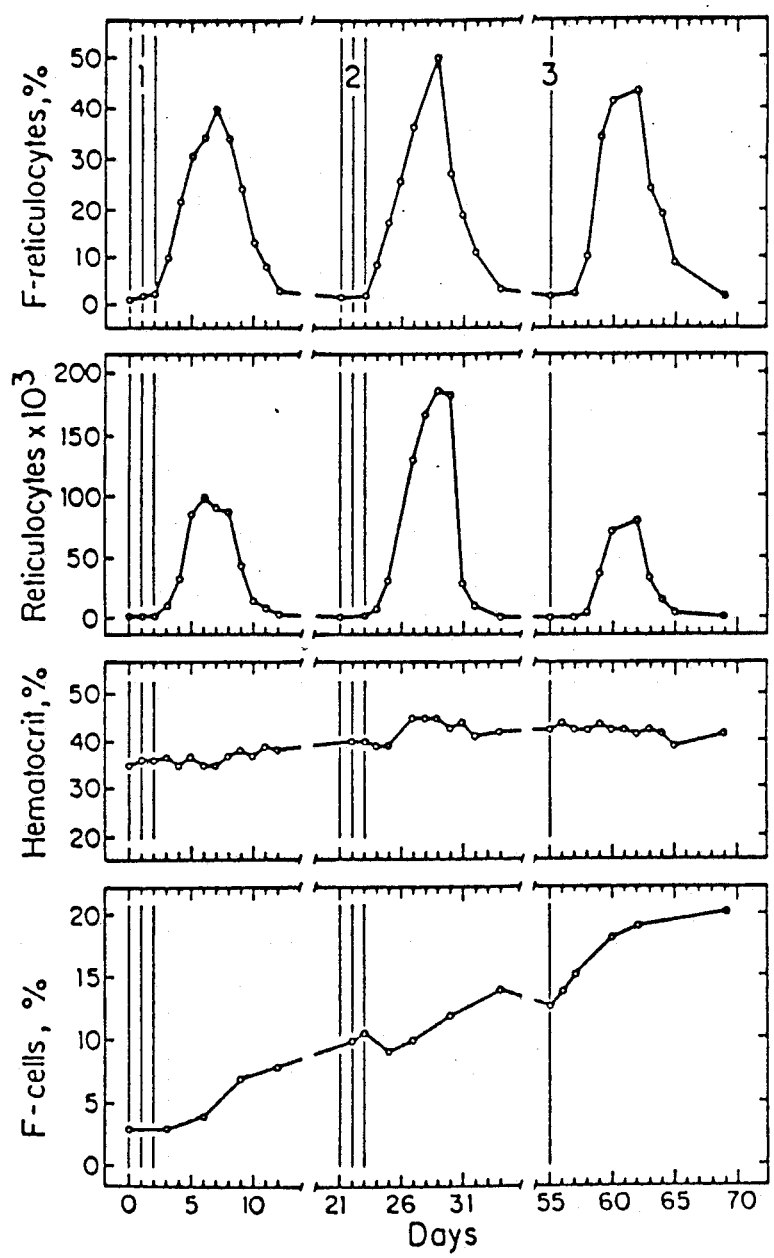
FIG. 2 shows results of sequentially treating a nonanemic baboon (animal B) with recombinant erythropoietin, first by intravenous injections of 1500 I.U./kg every 12 hours for 3 days (vertical lines 1), next with 3000 I.U./kg every 12 hours for 3 days (vertical lines 2), and finally with 3000 I.U./kg at time zero and again 12 hours later (vertical line 3)

Animal B was initially treated with 1500 I.U. rHuEpo/kg, twice a day for three days (FIG. 2, Treatment 1). This treatment produced a sharp increment in reticulocytes, which reached a maximum on day 6. F-reticulocytes were 0.8% on day 0 and 40% on day 7. The $\gamma/\gamma+\beta$ ratio increased from 0.01 to 0.15.

Animal B was subsequently treated with the same schedule (6 treatments in 3 days), except that 3000 l.U. rHuEpo/kg were used (FIG. 2, Treatment 2). Doubling the erythropoietin dose resulted in a substantial increase in absolute reticulocytes. F-reticulocytes were 2% before treatment and 50% at day 8 from the onset of this second treatment.

Animal B subsequently received a single-day treatment consisting of 2 injections of 3000 I.U. rHuEpo/kg each, given 12 hours apart (FIG. 2, Treatment 3). This treatment resulted in stimulation of F-reticulocyte production, the kinetics of which were as those of the two previous three-day treatments. A maximal F-reticulocyte value of 41.2% was achieved on day 7.

Referring to FIG. 2 in its entirety, note the sharp increment of F-reticulocyte formation produced by all the treatments and that the single-day treatment stimulated F-reticulocytes as efficiently as the three-day treatments. Furthermore, as a cummulative result of the three treatments, F-cells of animal B increased from 2.8% pretreatment to 20% by day 69.

Stimulation of F-cell formation in anemic animals

Figure 3:
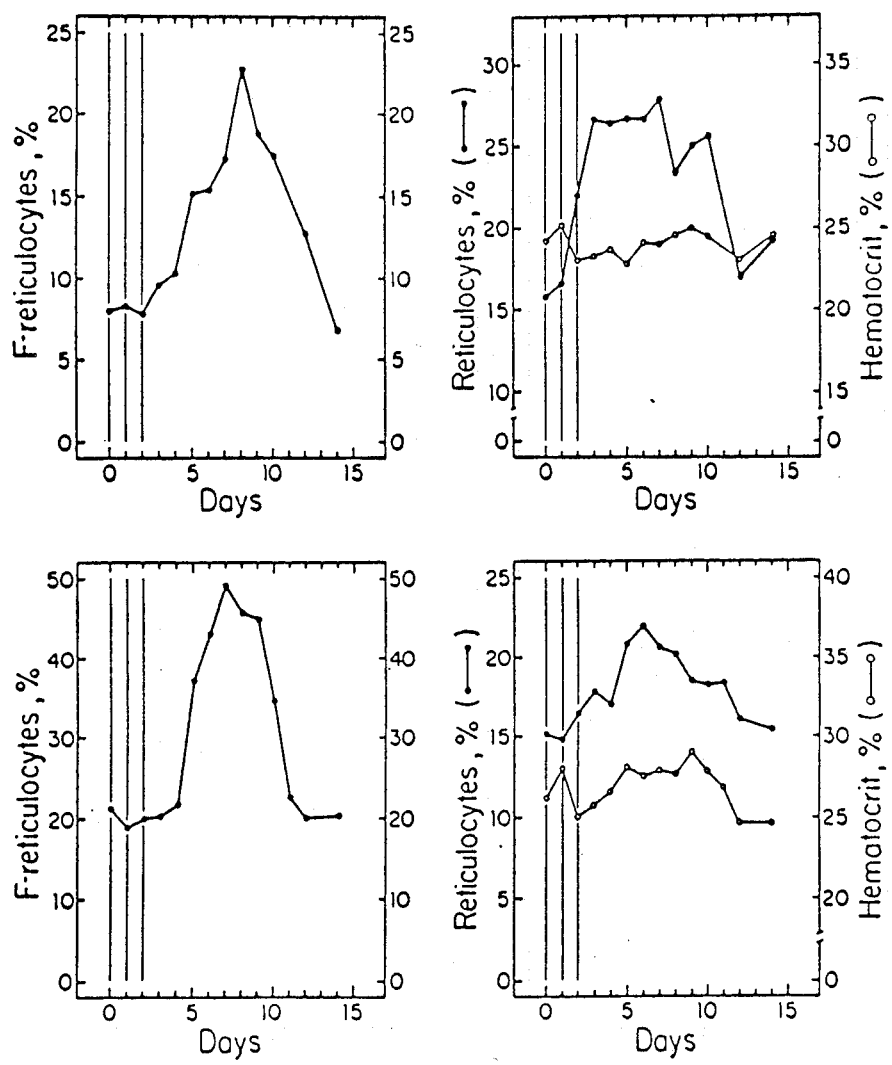
FIG. 3 shows stimulation of F-reticulocyte formation following administration of recombinant erythropoietin to two chronically anemic baboons (animals C and D, in upper and lower panels, respectively)

Animals C and D were kept chronically anemic (by daily phlebotomies) for approximately two months before the initiation of treatment. Hematocrits were kept at the range of 24-26% in animal C and 26-28% in animal D. The level of endogeneous erythropoietin (Epo) in animal C was 150 mU Epo/ml, and in animal D it was 220 mU/ml. Both animals were treated with of 3,000 I.U. rHuEpo/kg twice a day for 3 days, and they responded with increases in F-reticulocyte production. Results are shown in FIG. 3 for animal C (upper panels) and animal D (lower panels).

Administration of recombinant erythropoietin in animal C resulted in increase of F-reticulocytes from 6-8% pretreatment to 10.2% by day 4; by day 8, 22.8% of reticulocytes were F-cells. $\gamma/\gamma+\beta$ ratios increased from 0.02-0.03 before treatment to 0.10 by day 8.

Animal D initially had 18-20% F-reticulocytes at a steady state hematocrit of 26-28%. Treatment with recombinant erythropoietin resulted in elevation of F-reticulocytes to 49.7% by day 7. The $\gamma/\gamma+\beta$ ratio increased from 0.06 pretreatment to 0.24 by day 8.

These results demonstrated that pulse treatment with exogenous erythropoietin can stimulate fetal hemoglobin production even in animals with chronic anemia, high levels of endogenous erythropoietin, and an expanded erythropoiesis.

Kinetics of F-reticulocyte formation

Figure 4:
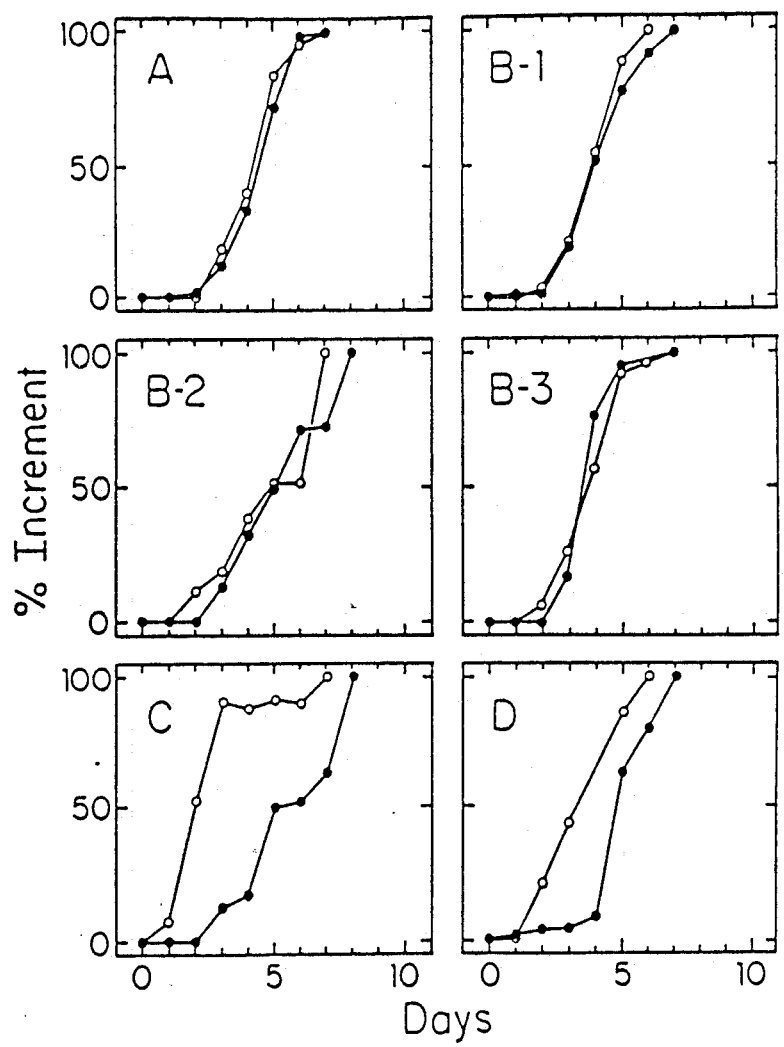
FIG. 4 compares the rates of increment of reticulocytes (open circles) and F-reticulocytes (solid circles) in animals A, B (for treatments 1, 2, and 3), C, and D; and, FIG. 5 compares the increments of reticulocytes (upper panel) and F-reticulocytes (lower panel) in the nonanemic (solid lines) and anemic (dashed lines) animals.

FIG. 4 shows the rates of increment of reticulocytes (open circles) and F-reticulocytes (solid circles) in animals A to D. Note the coincidence of reticulocyte and F-reticulocyte kinetics in the nonanemic animals (A and B) and the delayed appearance of F-reticulocytes in the two chronically anemic animals (C and D). The kinetics of F-reticulocyte production are consistent with the hypothesis that F-reticulocytes are derived from the mobilization of erythroid progenitors.

Figure 5:
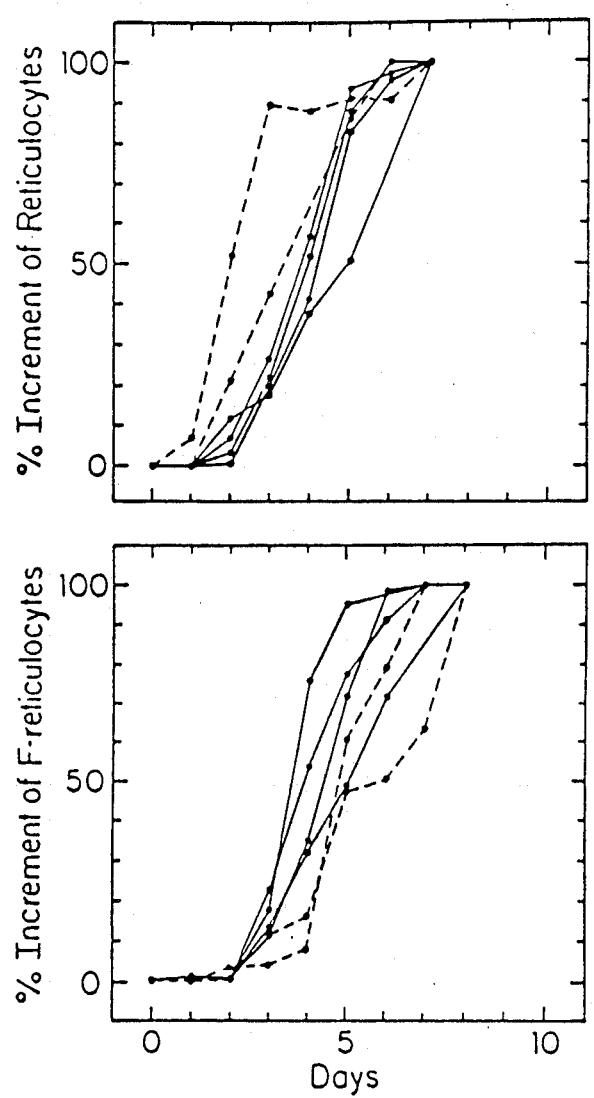

FIG. 5 compares the rates of reticulocyte (upper panel) and F-reticulocyte (lower panel) formation following administration of erythropoietin. In the nonanemic animals (solid lines), the rate of increment in reticulocytes coincided with the rate of increment in F-reticulocytes. Increments in F-reticulocytes appeared 3 days from the onset of treatment and peaked between days 6 and 8. Such kinetic responses are compatible with the interpretation that the bulk of F-reticulocytes derive from mobilization of the progenitor cell pool.

In the anemic animals (dashed lines), reticulocytosis appeared earlier than in the nonanemic animals; the increase in F-reticulocytes occurred two to three days after the appearance of reticulocyte response (FIGS. 4C and 4D). The earlier appearance of reticulocytosis in the anemic animals is attributed to the existence of an expanded pool of precursors and late progenitors on which erythropoietin can act. This pool is expected to have fewer cells capable of Hb F formation. Stamatoyannopoulos, G., et al., Ann. NY Acad. Sci. 1985, 445:188-197. The delayed (compared to reticulocytes) appearance of F-reticulocytes in the anemic animals provides further support to the notion that these F-cells are derived from the pool of earlier erythroid progenitors which are mobilized in response to the pulse dose of erythropoietin.

While preferred embodiments of the invention have been illustrated and described, it is to be understood that, within the scope of the appended claims, various changes can be made therein. Hence, the invention can be practiced in ways other than those specifically described herein.

The embodiments of the invention in which an exclusive property of privilege is claimed are defined as follows:

1. A method of obtaining an increase in F-reticulocyte production in a patient comprising treating the patient with a plurality of treatment regimens, each treatment regimen having a duration of from about 7 to about 20 days and comprising a first time period having a duration of about one to about three days wherein at least about 500 I.U. of erythropoietin per kg of body weight is administered to the patient and a second time period during which erythropoietin is withheld from the patient.

2. The method of claim 1 wherein each administration of erythropoietin comprises from about 500 to about 3000 I.U. of erythropoietin kg of body weight of the patient.

3. A method of obtaining an increase in F-reticulocyte production in a patient comprising treating the patient with a plurality of treatment regimens, each treatment regimen having a duration of from about 7 to about 20 days and comprising a first time period wherein at least about 500 I.U. of erythropoietin per kg of body weight is administered to the patient and a second time period during which the erythropoietin is withheld from the patient, and wherein the patient is additionally treated with a cell cycle specific drug selected from the group of hydroxyurea, cytarabine and 5-azacytidine.

4. The method of claim 1 wherein the amount of erythropoietin administered during the first time period is sufficient to increase F-reticulocyte formation in the patient by twofold.

5. The method of claim 1 wherein each of the treatment regimens individually has a duration of from about 10 to about 15 days.

6. The method of claim 1 wherein one or more of the first time periods in the treatment regimens has a duration of about one day.

7. The method of claim 1 wherein erythropoietin is administered at least twice during each first time period.

8. The method of claim 7 wherein erythropoietin is administered at from about 8 to about 24 hour intervals during each first time period.

9. The method of claim 8 wherein erythropoietin is administered at from about 12 to about 16 hour intervals during each first time period.

10. The method of claim 1 wherein each administration of erythropoietin comprises about 1500 I.U. erythropoietin per kg body weight of the patient.

11. The method of claim 1 wherein the erythropoietin is administered by intravenous or intramuscular injection.

12. The method of claim 1 wherein the erythropoietin is recombinant erythropoietin.

13. The method of claim 3 wherein the cell cycle specific drug is hydroxyurea.

* * * * *

UNITED STATES PATENT AND TRADEMARK OFFICE
CERTIFICATE OF CORRECTION

PATENT NO. : 4,965,251

DATED : October 23, 1990

INVENTOR(S) : G. Stamatoyannopoulos

Page 1 of 2

It is certified that error appears in the above-identified patent and that said Letters Patent is hereby corrected as shown below: ON TITLE PAGE:

| Column | Line | Error |
|---|---|---|
| [56] | | References cited, 7th reference, "incresing" should be --increasing-- |
| [56] | | References cited, 29th reference, "erythripoietin" should be --erythropoietin-- |
| [56] | | References cited, 29th reference, "quantative" should be --quantitative-- |
| [56] | | References cited, 37th reference, "48( ):843-852" should be --48(6):843-852-- |
| 1 | 22 | after "designated" insert --a-- |
| 1 | 44 | "erythrccytes" should be --erythrocytes-- |
| 2 | 36&37 | "53-2.Other" should be --532. Other-- |
| 3 | 2 | "80:310-312;" should be --180:310-312;-- |

UNITED STATES PATENT AND TRADEMARK OFFICE
CERTIFICATE OF CORRECTION

PATENT NO. : 4,965,251

DATED : October 23, 1990

INVENTOR(S) : G. Stamatoyannopoulos

It is certified that error appears in the above-identified patent and that said Letters Patent is hereby corrected as shown below:

| Column | Line | Error |
|---|---|---|
| 4 | 15 | "posttreatment" should be --post-treatment-- |
| 5 | 4 | after "about" insert --1-- |
| 6 | 53 | "o" should be --of-- |
| 7 | 2 | "On" should be --on-- |
| 7 | 3 | "Of" should be --of-- |
| 8 | 51 (Claim 2, line 3) | after "erythropoietin" insert --per-- |
| 8 | 57 (Claim 3, line 5) | after "period" insert --having a duration of about one to about three days) |

Signed and Sealed this

Twenty-sixth Day of May, 1992

*Attest:*

DOUGLAS B. COMER

*Attesting Officer*   *Acting Commissioner of Patents and Trademarks*